United States Patent [19]

Kubota et al.

[11] Patent Number: 4,770,881
[45] Date of Patent: Sep. 13, 1988

[54] PROCESS FOR PRODUCING VINEGAR

[75] Inventors: Terumasa Kubota, Toyohashi; Hiroyuki Kato, Miyakemachi; Shinji Tanijiri, Suita; Hiroki Matsuda, Sakai, all of Japan

[73] Assignee: Tamanoi Vinegar Corporation Limited, Osaka, Japan

[21] Appl. No.: 98,991

[22] Filed: Sep. 21, 1987

[30] Foreign Application Priority Data

Sep. 19, 1986 [JP] Japan .................. 61-221132

[51] Int. Cl.$^4$ .................. C12J 1/00; C12P 7/54
[52] U.S. Cl. .................. 426/17; 435/140; 426/495
[58] Field of Search ............. 426/7, 17, 127, 478–479, 426/495, 489–490, 493, 592; 435/140, 823, 161, 162

[56] References Cited

U.S. PATENT DOCUMENTS

| | | | |
|---|---|---|---|
| 2,224,059 | 12/1940 | Mostny | 426/17 |
| 4,456,622 | 6/1984 | Maselli et al. | 426/17 |
| 4,499,117 | 2/1985 | Bonneau | 426/592 |
| 4,581,236 | 1/1986 | Bandel et al. | 426/14 |
| 4,624,805 | 11/1986 | Lawhon | 530/376 |

Primary Examiner—Marianne Cintins
Attorney, Agent, or Firm—Wenderoth, Lind & Ponack

[57] ABSTRACT

A process for producing vinegar is disclosed wherein cereals or fruits are subjected to alcoholic fermentation thereby resulting in an alcohol fermentation product which is subsequently purified by ultra-filtration membranes to obtain purified alcohol. The purified alcohol is subjected to acetic acid fermentation and vinegar is recovered therefrom.

2 Claims, No Drawings

PROCESS FOR PRODUCING VINEGAR

BACKGROUND OF THE INVENTION

1. Field of the Invention

The present invention concerns a process for producing vinegar which comprises subjecting cereals or fruits as the starting material to alcohol fermentation, removing high molecular weight substances from alcohol fermentation products by treating the fermentation liquids by way of ultra-filtration membranes and then subjecting them to acetic acid fermentation.

2. Description of the Prior Art

In the production of vinegars, liquid filtrate obtained by primary filtration of fermentation products (hereinafter referred to as Moromis) after the completion of acetic acid fermentation have been filtered by using ultra-filtration membranes with the fractional molecular weight less than 50,000 thereby preventing the occurrence of secondary precipitation, preventing turbidity in the products and reducing the change of coloration (refer to Japanese Patent Application Laying Open No. Sho 61-242572).

Also, in the field of Sake and Soy sauce (Shoyu), a method has been known for the purification and filtration using ultra-filtration membranes in the final filtration. This method is applied for removing proteins that cause precipitation (Japanese Patent Publication No. Sho 60-23823).

Generally, alcohol Moromis obtained from cereals as the starting material contain high molecular weight substances, which cause bubbling in the aerated acetic acid fermentation and, further, cause precipitates during preservation of vinegar products after acetic acid fermentation.

According to the conventional production process for vinegar as described above, Moromis after the completion of the acetic acid fermentation are filtered by using ultra-filtration membranes with the fractional molecular weight of less than 50,000 thereby preventing occurrence of secondary precipitation, preventing the turbidity in the products and reduce the change of coloration. However, according to the prior art method, it can not prevent bubbling during aerated acetic acid fermentation. Then, although defoamers have generally been used for suppressing the bubbling in the aerated acetic acid fermentation, the defoaming effect obtained by this method is only temporary and not quite satisfactory.

SUMMARY OF THE INVENTION

The object of the present invention is to prevent the occurrence of precipitates during preservation of vinegar products, and conduct acetic acid fermentation at a good yield while suppressing the bubbling during aerated acetic acid fermentation, in which high molecular weight substances mainly composed of sugar and protein are removed from alcohol Moromis by applying purifying filtration using ultra-filtration membrane.

Specifically, the present invention provides a process for producing vinegar, which comprises subjecting cereals or fruits as the starting material to alcohol fermentation, applying purifying filtration to the thus obtained alcohol Moromis by way of ultra-filtration membranes thereby removing high molecular weight substances mainly comprising sugar and protein from alcohol Moromis and then subjecting it to acetic acid fermentation.

Precursors for the precipitates formed during preservation of vinegar products and substances causing bubbling during aerated acetic acid fermentation as the object of the present invention are high molecular weight substances mainly composed of sugar and protein. When the alcohol Moromis after the completion of alcohol fermentation (stock solution) and the liquid filtrates obtained from the stock solution by purifying filtration by the process according to the present invention are compared with respect to sugar and nitrogen ingredients, results are obtained which are shown in Table-1.

TABLE 1

|  | Alcohol | Total sugar | Total nitrogen | Amino form nitrogen |
|---|---|---|---|---|
| Stock solution | 8.1% | 700 mg/100 ml | 81 mg/100 ml | 38 mg/100 ml |
| Liquid filtrate | 8.1% | 400 mg/100 ml | 48 mg/100 ml | 30 mg/100 ml |
| Removal ratio | 0% | 43% | 41% | 21% |

The alcohol was measured by the analysis method specified by the Tax Administration Agency. The total nitrogen was measured by the Kierdahl method. The amino form nitrogen was measured by ninhydrin method. The total sugar was measured by the phenol sulfate method.

As shown in Table-1, it is recognized that the sugar and nitrogen ingredients are remarkably decreased by the process according to the present invention.

For confirming the occurrence of precipitates during the preservation of vinegar produced by the process according to the present invention, acetic acid fermentation was conducted by the usual method, the fermentation liquid was filtered with the addition of diatomaceous earth, preserved at 75° C. after removing bacterial, cell bodies, and occurrence of precipitates was tested. While vinegar produced by the conventional process with no filtration using ultra-filtration membranes, precipitates was recognized to be formed about ten days after the preservation, vinegar produced by the process according to the present invention showed no occurrence of precipitates even after the elapse of two months after the start of the preservation at all. Further, it gave less odors due to high molecular weight substances as compared with vinegar produced by the conventional process since the high molecular weight substances had previously been removed, and was excellent in the preferable flavor, it was recognized preferable in view of taste as shown in Table-2.

TABLE 2

|  | Those showing preference | Those not showing preference |
|---|---|---|
| Products by the present invention | 25 | 5 |
| Products by the prior art | 5 | 25 |

It has generally been considered that precipitates caused during the preservation of vinegar products are mainly composed of proteins which are insolubilized due to external factors such as preservation conditions, for example, temperature and light. Since the vinegars produced from alcohol Moromis removed with high molecular substances mainly composed of sugar and protein by the process according to the present invention caused no precipitates during preservation of the products, the present inventors have found that the precipitates comprise sugar and protein or the composite products thereof and, based on this finding, have accomplished the present invention of producing vinegar forming no precipitates during preservation by removing these high molecular weight substances contained in the alcohol Moromis by using ultra-filtration membranes.

Then, with an aim of prohibiting bubbling during aerated acetic acid fermentation, when the alcohol Moromis was purified by filtration using ultra-filtration membranes having various fractional molecular weights and defoaming test was conducted for the liquid filtrates, the results as shown in Table-3 were obtained. In the test, the liquid filtrates were placed in a predetermined bottle and shaken vigorously. The time required till the elimination of bubbles was measured.

TABLE 3

| No. | Fractional molecular weight | Result of defoaming test |
|---|---|---|
| 1 | Stock solution | ++ |
| 2 | 100,000 | ++ |
| 3 | 50,000 | + |
| 4 | 30,000 | ± about 10 sec |
| 5 | 10,000 | − |
| 6 | 6,000 | − |

Time required till the elimination of bubbles
− less than 10 seconds
+ from 10 to 60 seconds
++ more than 60 seconds From the results of Table-3, since it was considered that bubbling in the aerated acetic acid fermentation was caused by the high molecular substances with the molecular weight of greater than 30,000, aerated acetic acid fermentation was actually conducted for each of the liquid filtrates in a 5 liter volume fermentation vessel, and the bubbling state upon fermentation was compared. As the result, while fermentation was completed with no bubbling at all for Moromis No. 5 and No. 6 not containing the high molecular substances with the molecular weight greater than 10,000 in the same way as in Table-3, bubbles were recognized for No. 1–3 and addition of the defoamer was required. As for No. 4, some bubbles were observed, but fermentation was completed without defoamer. Accordingly, it was supposed that the high molecular substances with the molecular weight of nearly 30,000 cause bubbles.

Since vinegar prepared from cereals or fruits as the starting material contain high molecular weight substances, it is liable to cause precipitations during preservation of vinegar products thereby causing a reduction in the product quality. This gives a hindrance to the production of natural vinegar composed of 100% cereals instead of alcohol vinegar starting from industrial alcohol. However, according to the present invention, since the high molecular substances are eliminated from alcohol Moromis by the ultra-filtration membranes, vinegars prepared from Moromis as the starting material cause no precipitates and are excellent in preferable flavour and the series of purifying steps can be simplified. Furthermore, there are also recognized various effects that vinegar can be obtained at high yield since no bubbling is caused during aerated acetic acid fermentation.

DESCRIPTION OF EXAMPLES

EXAMPLE 1

To 2 kg of corn pulverizates (grain size of 42 mesh pass), 5.4 liter of water and 4 g of glucoamylase agent were added and then suspended by stirring. Then, pH value was adjusted to 4.5 with fumaric acid and 10 g of living yeast was added to conduct alcohol fermentation at 30° C. for 5 days.

1.6 liter of water was added to 6.2 liter of the resultant Moromis (alcohol concentration at 12.6%) to adjust the alcohol concentration to 10%, to which 2 liter of seed vinegar (10% acidity) was added to obtain 9.8 liter of alcohol Moromis.

The alcohol Moromis were subjected to solid-liquid separation by using a press type solid-liquid separation device to obtain 9.0 liter of alcohol Moromis at 8.1% alcohol concentration and 2.1% acidity.

The alcohol Moromis were purified by filtration using ultra-filtration membranes with the fractional molecular weight of 6,000 at 25° C. and under the condition of filtration pressure of 1.8 kg/cm$^2$ to obtain 8.8 liter of liquid filtrate (8.1% alcohol concentration and 2.1% acidity) (hereinafter referred to vinegar Moromis).

The vinegar Moromis were charged to 2 liter of active acetobactor-containing seed vinegar (8.0% acidity and 2.5% alcohol) previously cultured by aerated acetic acid fermentation in a fermentation device and then acetic acid fermentation was conducted. Finally, 10.8 liter of fermentation liquids at 10.2% acidity was obtained. The resultant vinegar formed no precipitates during preservation and was excellent in the flavour. Further, no bubbling was caused during aerated acetic acid fermentation and the fermentation was completed at a good yield.

EXAMPLE 2

To 1 kg of corn pulverizates (grain size of 42 mesh pass), 2.7 liter of water and 2 g of glucoamylase agent were added and then suspended by stirring. Then, pH value was adjusted to 4.5 with fumaric acid and 5 g of living yeast was added to conduct alcohol fermentation at 30° C. for 5 days. 5.2 liter of alcohol Moromis (8.0% alcohol concentration) obtained after denaturation, and filtration under pressure were filtered using ultra-filtration membranes with fractional molecular weight of 10,000 under the condition at 25° C. and 3.0 kg/cm$^2$ of filtration pressure to obtain 5.0 liter of liquid filtrates (8.0% alcohol concentration). Then, 0.5 liter of water was added to make up the concentrated 0.2 liter of liquid (8.0% alcohol concentration) making into 0.7 liter in the total volume (2.3% alcohol concentration), which was again filtered using ultra-filtration membranes under the same conditions to obtain 0.5 liter of liquid filtrates (2.3% alcohol concentration). The resultant liquid filtrates were joined to prepare 5.5 liter of Moromis at 7.5% alcohol concentration and 1.5% acidity (hereinafter referred to as vinegar Moromis). 2.0 liter of the vinegar Moromis were charged to 2.0 liter of acetobactor-containing seed vinegar previously cultured by the aerated fermentation (1.5% alcohol concentration and 7.5% acidity), and acetic acid fermentation was conducted. 3.5 liter of vinegar Moromis were further charged when the acidity was increased to 7.5% and the acetic acid fermentation was continued. The fermentation was completed at 8.8% acidity and 7.5 liter of liquid volume and bacteria cell bodies were removed by filtration using diatomaceous earth. The resultant vinegar formed no precipitates during preservation and was excellent in flavour.

Further, no bubbling was caused during aerated acetic acid fermentation and the fermentation was completed at a good yield.

EXAMPLE 3

After immersing 1 kg of pulverized rice (grain size of 42 mesh pass) in 2.7 liter of water, liquefying enzyme was added thereto to liquefy at 60° C. for 30 min and, after processing them in an autoclave at 110° C. for 5 minutes, saccharifying enzyme was added and saccharification was conducted at 55° C. for 17 hours. Then, living yeast was added and alcohol fermentation was conducted at 30° C. for 5 days. 5.2 liter of alcohol Moromis (8.0% alcohol concentration) obtained after denaturation and filtration under pressure were filtered using ultra-filtration membranes with fractional molecular weight of 10,000 under the condition at 25° C. and 3.0 kg/cm$^2$ to obtain 5.0 liter of liquid filtrates. 0.5 liter of water was added to 0.2 liter of liquid concentrates, filtered again through the ultra-filtration membranes to obtain 0.5 liter of liquid filtrates. The resultant liquid filtrates were joined and aerated acetic acid fermentation was conducted in the usual way, to obtain vinegar at 8.8% acidity. The resultant vinegar showed less odor as compared with the vinegar prepared by the conventional method and formed no precipitates at all during preservation. Further, no bubbling was caused during the aerated acetic acid fermentation and the fermentation was completed at a good yield.

EXAMPLE 4

3.3 liter of water was added to 2 kg of concentrated apple juice, and alcohol fermentation was conducted by adding living yeast at 30° C. for 5 days. 7.5 liter of alcohol Moromis obtained after denaturation and filtration under pressure were filtered by using ultra-filtration membranes with the fractional molecular weight of 10,000 to obtain 7.3 liter of alcohol. The resultant alcohol was subjected to aerated acetic acid fermentation in the usual way, to obtain apple vinegar. The vinegar was of high commercial quality with no precipitates during preservation.

What is claimed is:

1. A process for producing vinegar, which comprises subjecting cereals or fruits to alcohol fermentation whereby an alcohol fermentation product containing sugar and protein high molecular weight substances is obtained, purifying the obtained alcohol fermentation product by ultra-filtration using ultra-filtration membranes which are sufficient to remove said sugar and protein high molecular weight substances from the alcohol fermentation product to produce a purified alcohol, subjecting the purified alcohol to acetic acid fermentation whereby an acetic acid fermentation product is obtained, and recovering vinegar from the acetic acid fermentation product.

2. A process for producing vinegar as defined in claim 1, wherein the sugar and protein high molecular weight substances removed have molecular weights of greater than 30,000.

* * * * *